US00PP23653P2

(12) United States Plant Patent
Tanaka et al.

(10) Patent No.: US PP23,653 P2
(45) Date of Patent: Jun. 11, 2013

(54) ROSE PLANT NAMED 'FLORIROSAVIO04'

(50) Latin Name: *Rosa hybrida*
Varietal Denomination: Florifosavio04

(75) Inventors: Yoshikazu Tanaka, Shiga (JP); Yukihisa Katsumoto, Osaka (JP); Yuko Fukui, Takatsuki (JP)

(73) Assignee: Suntory Flowers Ltd., Tokyo (JP)

( * ) Notice: Subject to any disclaimer, the term of this patent is extended or adjusted under 35 U.S.C. 154(b) by 395 days.

(21) Appl. No.: 12/925,948

(22) Filed: Nov. 2, 2010

(51) Int. Cl.
*A01H 5/00* (2006.01)

(52) U.S. Cl.
USPC ..... Plt./130

(58) Field of Classification Search
USPC ..... Plt./130
See application file for complete search history.

*Primary Examiner* — Annette Para
(74) *Attorney, Agent, or Firm* — C. A. Whealy

(57) ABSTRACT

A new and distinct cultivar of Rose plant named 'Florirosavio04', characterized by its upright flowering stems; vigorous growth habit; freely branching plant habit; and strongly fragrant flowers that are light violet in color.

1 Drawing Sheet

Botanical designation: *Rosa hybrida.*
Cultivar denomination: 'FLORIFOSAVIO04'.

BACKGROUND OF THE INVENTION

The present Invention relates to a new and distinct cultivar of Rose plant, botanically known as *Rosa hybrida*, commercially used as a cut flower Rose plant and hereinafter referred to by the name 'Florirosavio04'.

The new Rose plant is a product of a planned breeding program conducted by the Inventors in Katori-shi, Chiba-ken, Japan. The objective of the breeding program was to develop new vigorous and fragrant cut flower Rose varieties with novel and attractive flower colors and excellent postproduction longevity.

The new Rose plant is a naturally-occurring whole plant mutation of *Rosa hybrida* 'KElhaburu', disclosed in U.S. Plant Pat. No. 19,509. The new Rose plant was discovered and selected by the Inventors as a single plant within a population of plants of 'KElhaburu' in a controlled greenhouse environment in Katori-shi, Chiba-ken, Japan.

Asexual reproduction of the new Rose plant by cuttings in a controlled environment in Katori-shi, Chiba-ken, Japan has shown that the unique features of this new Rose plant are stable and reproduced true to type in successive generations of asexual reproduction.

SUMMARY OF THE INVENTION

Plants of the new Rose have not been observed under all possible environmental conditions. The phenotype may vary somewhat with variations in environment such as temperature and light intensity, without, however, any variance in genotype.

The following traits have been repeatedly observed and are determined to be the unique characteristics of 'Florirosavio04'. These characteristics in combination distinguish 'Florirosavio04' as a new and distinct Rose plant:

1. Upright flowering stems.
2. Vigorous growth habit.
3. Freely branching plant habit.
4. Strongly fragrant flowers that are light violet in color.

Plants of the new Rose differ from plants of the parent, 'KElhaburu' primarily in flower color as plants of 'KElhaburu' have violet blue-colored flowers.

Plants of the new Rose can be compared to plants of Rose 'Lavande', not patented. In side-by-side comparisons conducted in Katori-shi, Chiba-ken, Japan, plants of the new Rose had larger flowers than plants of 'Lavande'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the top of the sheet comprises a side perspective view of typical flowering plants of 'Florirosavio04' grown in ground beds.

The photograph at the bottom of the sheet is a close-up view of typical flowers of 'Florirosavio04'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in ground beds in a glass-covered greenhouse in Katori-shi, Chiba-ken, Japan and under typical commercial Rose production practices. Plants were one year old when the photographs and description were taken. In the following description, color references are made to The Royal Horticultural Society Colour Chart, 2001 Edition, except where general terms of ordinary dictionary significance are used.

Botanical classification: *Rosa hybrida* 'Florirosavio04'.

Parentage: Naturally-occurring whole plant mutation of *Rosa hybrida* 'KElhaburu', disclosed in U.S. Plant Pat. No. 19,509.

Propagation:

*Type*.—By cuttings.

*Root description*.—Fibrous, medium in thickness.

*Rooting habit*.—Freely branching; moderately dense.

Plant description:

*Plant form*.—Upright plant habit with upright flowering stems.

*Growth habit*.—Vigorous growth habit; freely branching habit; dense and bushy plant form.

*Plant height*.—About 100 cm to 120 cm.

*Plant width* (*spread*).—About 60 cm to 80 cm.

*Stem texture*.—Smooth, glabrous.

*Stem color, new wood*.—Close to 146D.

*Stem color, old wood*.—Close to 137A.

*Thorns*.—Density: About 10 to 13 thorns per 15 cm of stem. Shape: Roughly triangular with hooked acuminate apices. Height: About 5 mm to 6 mm. Color, immature: Close to 178A. Color, mature: Close to 165A.

Foliage description:

*Arrangement*.—Alternate; compound with typically five leaflets per leaf.

*Leaf length*.—About 13 cm.

*Leaf width*.—About 10 cm.

*Leaflet length*.—About 5 cm.

*Leaflet width*.—About 3 cm.

*Leaflet shape*.—Ovate.

*Leaflet apex*.—Acuminate.

*Leaflet base*.—Rounded.

*Leaflet margin*.—Serrate.

*Leaflet texture, upper and lower surfaces*.—Smooth, glabrous; leathery.

*Leaflet venation pattern*.—Pinnate, reticulate.

*Leaflet color*.—Developing leaflets, upper and lower surfaces: Close to 178A. Fully expanded leaflets, upper surface: Close to 139A; venation, close to 137D. Fully expanded leaflets, lower surface: Close to 147B; venation, close to 137D.

*Petioles*.—Length: About 2 mm to 3 mm. Texture, upper and lower surfaces: Smooth, glabrous. Color, upper and lower surfaces: Close to 137D.

*Stipules*.—Quantity/arrangement/appearance: Two, adnate to the petiole, leafy. Length: About 9 mm to 11 mm. Shape: Roughly deltoid.

Flower description:

*Flower type and form*.—Symmetrical rosette flowers borne singly or in clusters of five to seven flowers; when opening, flowers are high-centered and become flatten with development with outer petals recurving.

*Flowering habit*.—Year-round under greenhouse conditions; flowering continuous.

*Flower longevity*.—On the plant, flowers last about six to seven days; as a cut flower, flowers last about seven to eight days; petals not persistent.

*Flower diameter*.—About 8 cm to 9 cm.

*Fragrance*.—Strongly fragrant; sweet, pleasant.

*Flower buds*.—Shape: Pointed ovoid. Length: About 3 cm. Diameter: About 2 cm. Color: Close to 77B.

*Petals*.—Quantity per flower: About 20 to 25; petals imbricate. Shape: Obcordate to orbicular. Apex: Rounded or occasionally notched; apices slightly recurved. Base: Rounded. Margin: Entire. Texture, upper and lower surfaces: Smooth, glabrous. Color: Upper surface: Close to 85A; towards the base there is a small spot, close to 154D; color becoming closer to 85B with development; guard petals have occasional longitudinal streaks, close to 138D. Lower surface: Close to 76C.

*Petaloids*.—Quantity per flower: If present, one or two. Shape: Irregular. Margin: Entire. Texture, upper and lower surfaces: Smooth, glabrous. Color, upper and lower surfaces: Close to 85A.

*Sepals*.—Quantity per flower: Typically five. Length: About 2 cm to 2.4 cm. Width: About 6 mm to 7 mm. Shape: Lanceolate. Apex: Tapered. Base: Truncate. Margin: Entire; ciliate. Texture, upper and lower surfaces: Pubescent. Color, upper surface: Close to N138C. Color, lower surface: Close to 146B.

*Peduncles*.—Length: About 4 cm to 5 cm. Diameter: About 6 mm to 7 mm. Strength: Stiff, erect. Texture: Smooth, glabrous. Color: Close to 146C.

*Reproductive organs*.—Receptacle: Height: About 8 mm. Diameter: About 8 mm. Texture: Smooth, glabrous. Color: Close to 146C. Stamens: Quantity: About 70 to 85 per flower. Length: About 8 mm to 11 mm. Filament length: About 5 mm to 8 mm. Filament color: Close to 8D. Anther length: About 3 mm. Anther shape: Reniform. Anther color: Close to 21D. Pollen color: Close to 22A. Pistils: Quantity: About 45 to 55 per flower. Length: About 4 mm to 5 mm. Style length: About 3 mm to 4 mm. Style color: Close to 155C. Stigma length: About 1 mm. Stigma color: Close to 159A. Hips: Diameter: About 2.5 cm to 2.8 cm. Shape: Round. Texture: Smooth. Color: Close to 16A. Seeds: Quantity per hip: About 10 to 16. Length: About 3 mm to 4 mm. Diameter: About 3 mm to 4 mm. Texture: Smooth. Color: Close to 22D.

Pathogen/pest resistance: Plants of the new Rose have been observed to be resistant to Rust. Plants of the new Rose have not been observed to be resistant to pests and other pathogens common to Roses.

Hardiness: Plants of the new Rose have been observed to be hardy to USDA Hardiness Zone 6.

It is claimed:

1. A new and distinct Rose plant named 'Florirosavio04' as illustrated and described.

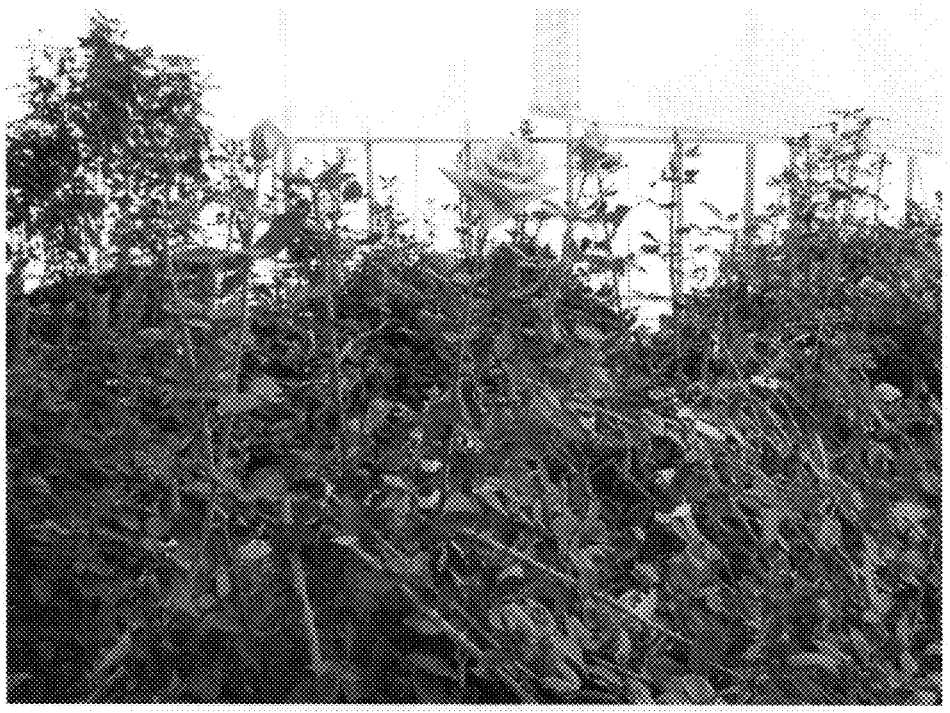
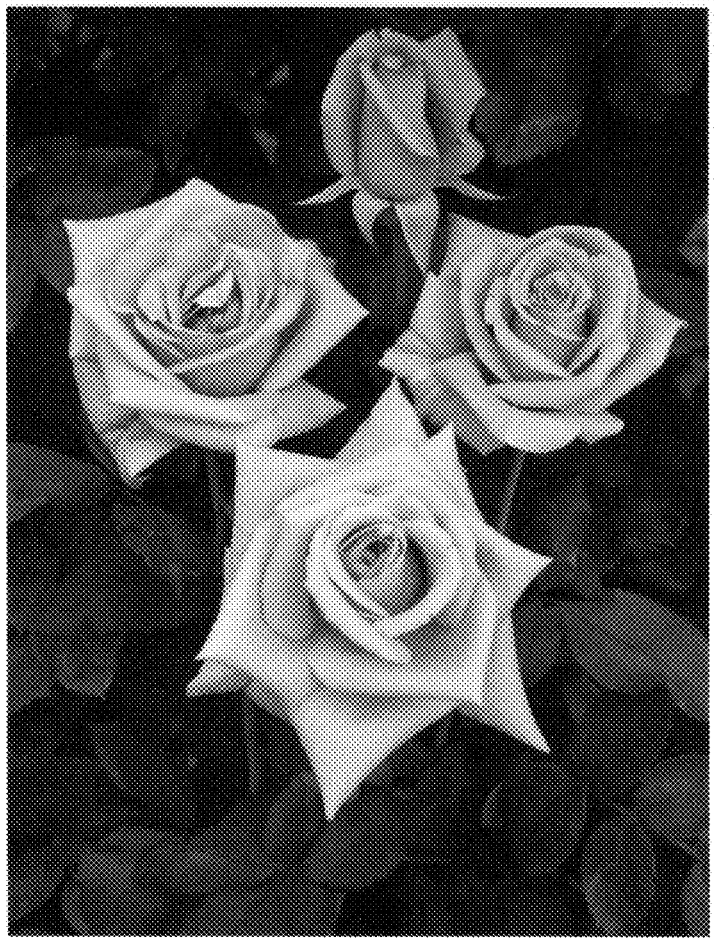

* * * * *